United States Patent [19]

Croset et al.

[11] 4,364,226
[45] Dec. 21, 1982

[54] DEVICE FOR INSERTING A SENSOR INTO THE EXHAUST CONDUITS OF AN INTERNAL COMBUSTION ENGINE AND A FUEL-CONTROL SYSTEM USING SUCH A DEVICE

[75] Inventors: Michel Croset; Gonzalo Velasco, both of Paris, France

[73] Assignee: Thomson-CSF, Paris, France

[21] Appl. No.: 186,846

[22] Filed: Sep. 15, 1980

[30] Foreign Application Priority Data

Sep. 14, 1979 [FR] France .................. 79 22986

[51] Int. Cl.³ .............. F01N 7/18; G01N 27/28; G01K 1/14
[52] U.S. Cl. .............................. 60/276; 60/277; 73/25; 204/195 S; 285/93; 374/144
[58] Field of Search ......... 285/93; 204/195 S, 195 R; 73/346, 25; 60/276, 277; 339/10, 15

[56] References Cited

U.S. PATENT DOCUMENTS

| | | | |
|---|---|---|---|
| 651,326 | 6/1900 | Fowler | 339/15 |
| 2,496,154 | 1/1950 | Fermier | 285/93 |
| 3,154,060 | 10/1964 | Hundere | 73/346 |
| 3,314,039 | 4/1967 | Opper | 339/15 |
| 3,851,469 | 12/1974 | Eichler | 60/288 |
| 3,939,711 | 2/1976 | Hanaoka | 73/346 |
| 3,968,689 | 7/1976 | Leshner | 73/346 |
| 4,024,850 | 5/1977 | Peter | 60/277 |
| 4,157,785 | 6/1979 | Freliech | 339/17 LC |
| 4,208,266 | 6/1980 | Auman | 204/195 S |

*Primary Examiner*—Douglas Hart
*Attorney, Agent, or Firm*—Oblon, Fisher, Spivak, McClelland & Maier

[57] ABSTRACT

A device for inserting a sensor into the exhaust conduits of an internal combustion engine, wherein the support of the sensor is formed by the sealing element of the assembly gaskets of these exhaust conduits. In accordance with a first variation the sensor is inserted by means of the gasket located between the manifold and the exhaust pipe, and in accordance with a second variation the sensor is inserted by means of the gasket located between the cylinder head and the exhaust manifold. This gasket may comprise several sensors, one per exhaust port. The sensor to be inserted may in particular be of the electrochemical collector type comprising a measuring cell of the concentration-stack type.

8 Claims, 11 Drawing Figures

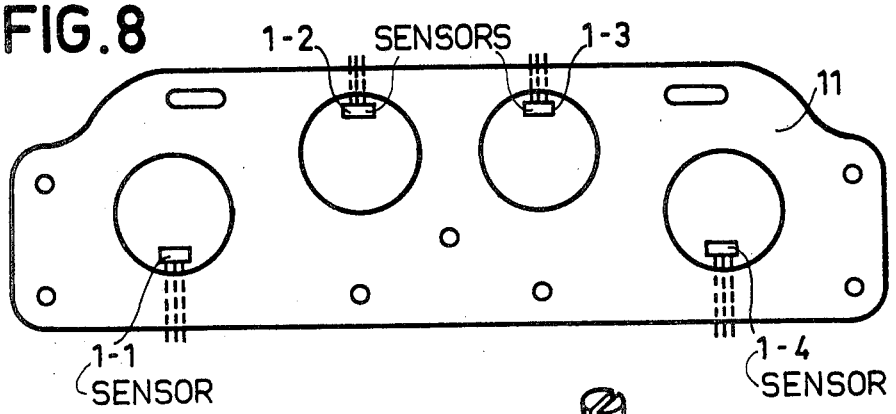
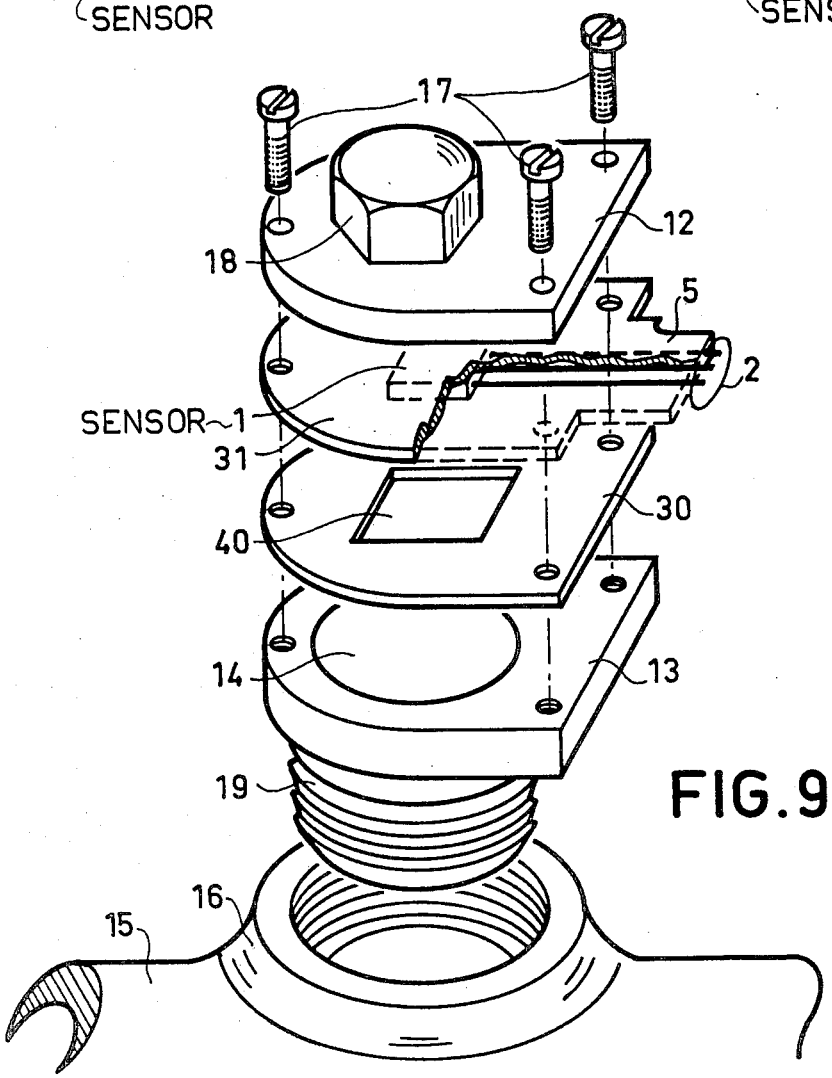

DEVICE FOR INSERTING A SENSOR INTO THE EXHAUST CONDUITS OF AN INTERNAL COMBUSTION ENGINE AND A FUEL-CONTROL SYSTEM USING SUCH A DEVICE

BACKGROUND OF THE INVENTION

The invention relates to a device for inserting a sensor into the exhaust conduits of an internal combustion engine, and in particular a sensor of the electrochemical type collecting concentrations of species in the exhaust gases.

Such sensors are still called probes λ. Their voltage response curves show a sudden swing at the stoichiometry of the fuel-air mixture whose relative concentrations in the exhaust gases it is desired to measure. The analysis is effected by taking samples of exhaust gases which alone are admitted inside the sensor (where they are brought to a thermodynamic balance), in accordance with the so-called "test sampling" technique. To reach this result means for limiting the gaseous exchange are usually disposed upstream of the sensor. The electric signals delivered by such a sensor are then used by a regulation system for modifying, for example, the air-fuel proportion admitted into the cylinders of a combustion engine. This regulation method is well-known in the automobile electronics field.

These sensors have been constructed with different approaches: in accordance with a first earlier approach, the active element or measuring cell, generally of the concentration-stack type, has a so-called "glove finger" structure; in accordance with a second approach, the active part of the sensor is formed by thin or thick-film depositing techniques used in the manufacture of semiconductor circuits, and presents a flat structure.

In all cases, the measuring cell must be inserted into the exhaust conduits of a combustion engine in which it is desired to analyze the composition of the exhaust gases. For this, according to the prior art, the measuring cell is inserted into a case having the general structure of a sparking plug. This case must provide, on the one hand, an absolute seal between a first enclosure, or measuring enclosure, in contact with the gases to be analyzed and a second so-called reference enclosure and, on the other hand, provide the electrical connections between the measuring cell and external circuits using the electrical signals delivered. These different requirements lead to a complex and relatively costly structure. Furthermore, insofar as the second approach is concerned, the flat geometry of the measuring cell must be adapted to the cylindrical geometry of the case. Finally, some more recent sensors comprise more than two electrical connections, but the structures of cases of the sparking-plug type do not lend themselves very well to bringing out more than two connections.

In addition to the difficulties which have just been pointed out, allowance must also be made for the need for transforming existing exhaust conduits as to be able to insert therein by screwing the case containing the measuring cell. Finally, since the type of sensor which has just been described may present a high output impedance, the insulators must be of a good quality, and this at a high temperature, which is difficult to obtain.

SUMMARY OF THE INVENTION

To palliate these disadvantages, the invention provides an insertion device particularly adapted to small-size sensors having a flat structure, comprising possibly more than two output connections, this device using only simple and cheap components. To this end, the invention makes use of the presence of connection and sealing gaskets existing in all the exhaust conduits, these gaskets being either the gaskets between the exhaust ports provided in the cylinder head of an engine and the exhaust manifold, or the gasket between this manifold and the exhaust pipe leading to the different silencers and exhaust chamber.

The invention provides then a device for inserting at least one sensor into the exhaust conduits of an internal combustion engine comprising a cylinder head having at least one exhaust port; this sensor being designed to measure at least one of the significant parameters of the exhaust gases flowing at high temperature in the exhaust conduits, and developing at the output connections electrical signals representative of these parameters; said device being principally characterized in that it comprises, forming a support for the sensor, a flat element of small thickness formed by at least one sheet of insulating and compressible material, resistant to the high temperatures, and having therethrough at least one communication window letting the exhaust gases pass freely therethrough, said window being provided in a central region of this element where is positioned the sensor held by its connections; and in that, with the element inserted between two assemblies of mechanical pieces coupled together by fixing means, the element forms a gas-tight assembly gasket with respect to the exhaust gases.

The invention further provides a regulating device for controlling the amount of fuel in a combustion engine comprising several cylinders associated with an insertion device comprising one sensor per cylinder, in which the output signals of the sensors are used for controlling the amount of fuel.

DESCRIPTION OF THE DRAWINGS

The invention will be better understood and other characteristics will appear from reading the following description with reference to the accompanying drawings in which:

FIGS. 4 to 8 illustrate several embodiments of the invention in accordance with a first approach;

FIG. 9 illustrates a second approach of the invention;

DESCRIPTION OF THE PREFERRED EMBODIMENTS

Figure 1:
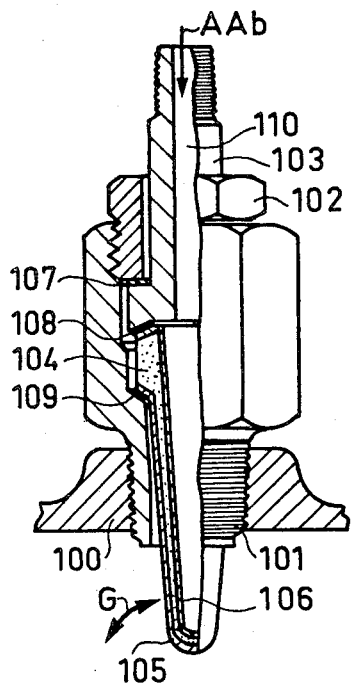
FIGS. 1 and 2 illustrate devices for inserting a sensor in an exhaust pipe in accordance with the prior art.

The devices for inserting sensors into the exhaust conduits of an internal combustion engine in accordance with the prior art have in general a structure similar to that of the sparking plugs of these engines. In accordance with a first earlier approach, the measuring cell properly speaking has a so-called "glove finger" shaped structure. Such a structure is illustrated in FIG. 1: the cell comprises two electrodes 105 and 106 deposited on each side of a solid electrolyte 104, for example lime-stabilized zirconia, electrolyte 104 providing the mechanical rigidity of the measuring cell. The unit is placed in a metal case 101 having a cylindrical structure designed for inserting the sensor by screwing into an exhaust conduit 100 so that the measuring cell is placed in contact with the exhaust gases G. For this type of sensor, the inside of the glove finger forms the reference compartment into which is brought by conduit 110, formed in a second metal piece 103, a reference gas which is in general formed by the ambient air A $A_b$. The case must provide, on the one hand, the seal and, on the other hand, the electrical connections between the electrodes 105 and 106 and external circuits using the signals delivered by the measuring cell. For this, the metal piece 103 ensures in cooperation with the conducting seal 108 a first electrical contact. A seal 109, also conducting, provides with case 101 in which is screwed a third metal piece 102 the second electrical contact. An insulating seal 107 provides electrical decoupling of metal pieces 102 and 103. The whole has a relatively complex structure, risking compromising the general reliability of the device; the most critical points being formed by seals 107 and 109. It should be recalled here that the environmental conditions of devices cooperating in the operation of an internal combustion engine are very severe. To the pressure differences between the gas flowing in the exhaust pipe and the atmosphere are added very considerable differences of temperature: inside the pipe, the exhaust gas generally reaches a temperature of the order of 800° C., the temperature being only of the order of 200° C. on piece 102 and a temperature slightly higher than the ambient temperature at the level of the input orifice of pipe 110. Furthermore, the device is subjected to considerable vibration. Finally all these stresses cause not only damage to the constituent elements of the case, but also damage to the measuring cell properly speaking: the stresses may in particular create cracks in the solid electrolyte.

Figure 2:
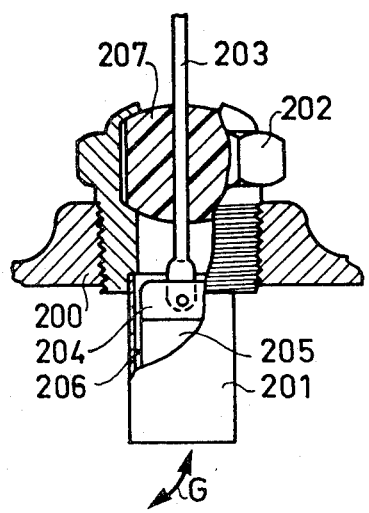

Therefore there have been more recently proposed electrochemical measuring cells constructed by the thin or thick-film depositing techniques. The cells thus formed are in general of the internal reference type. It is a question of measuring cells one of whose electrodes combines the electrode function and the reference medium function. For this an electrode is used based on a combination of the type: M-MX where M is a metal and X a halogen to be detected (for example M-MO in the case of detection of oxygen, and particularly in the exhaust gases). A sensor of this type and its case are illustrated in FIG. 2. A sensor, one of whose electrodes 205 can be seen in the figure, is force-fitted into a case 201 forming an electrical contact 206 with this electrode. The other electrode which is not visible is connected to the outside by an electrical connection 203. The unit is placed in a case 202 designed for inserting the sensor thus formed into an exhaust conduit 200 by screwing. The case also comprises an insulating material 207 providing simultaneously sealing of the sensor between the external medium and the inside of the exhaust pipe. In this approach, although the measuring cell has higher reliability, it is necessary to adapt a flat geometry, that of the cell, to a cylindrical geometry, that of the case. Furthermore, the two approaches present the disadvantage of requiring transformation in existing exhaust conduits. Finally, some sensors are fitted with more than two electrical connections and norms adopted by some constructors impose a "mechanical mass" distinct from the "electrical mass". The above-described cases are ill-adapted to these configurations.

Figure 3:
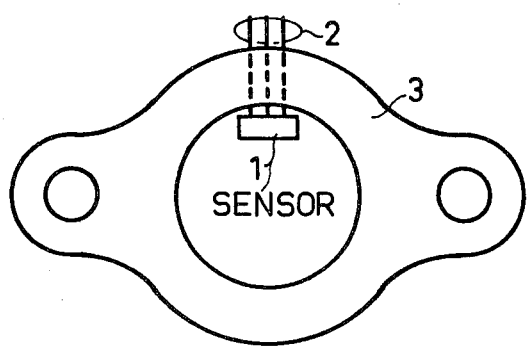
FIG. 3 illustrates schematically a device for inserting a sensor in accordance with the invention.

The invention provides on the contrary simplified insertion devices making use of certain elements existing in all the exhaust pipes of the internal combustion engines at present in use. The device for inserting a sensor in accordance with the invention is shown schematically in FIG. 3. In fact, for connecting two exhaust conduits together or an exhaust conduit with the exhaust ports formed in the cylinder head of an internal combustion engine, gaskets, generally made from asbestos, are used to provide the seal and having a good resistance at high temperatures. Furthermore the materials used, moreover generally inexpensive, are good insulators. These gaskets may then form an appropriate support for inserting a sensor, shown under the reference 1, into the exhaust conduits. This sensor has output connections 2, three in number in the figure. This number may be any number whatever. The sensor is maintained in the presence of the exhaust gas by the rigidity of these connections hemmed in the material of element 3 which forms a seal between two component parts of the exhaust system.

Figure 4:
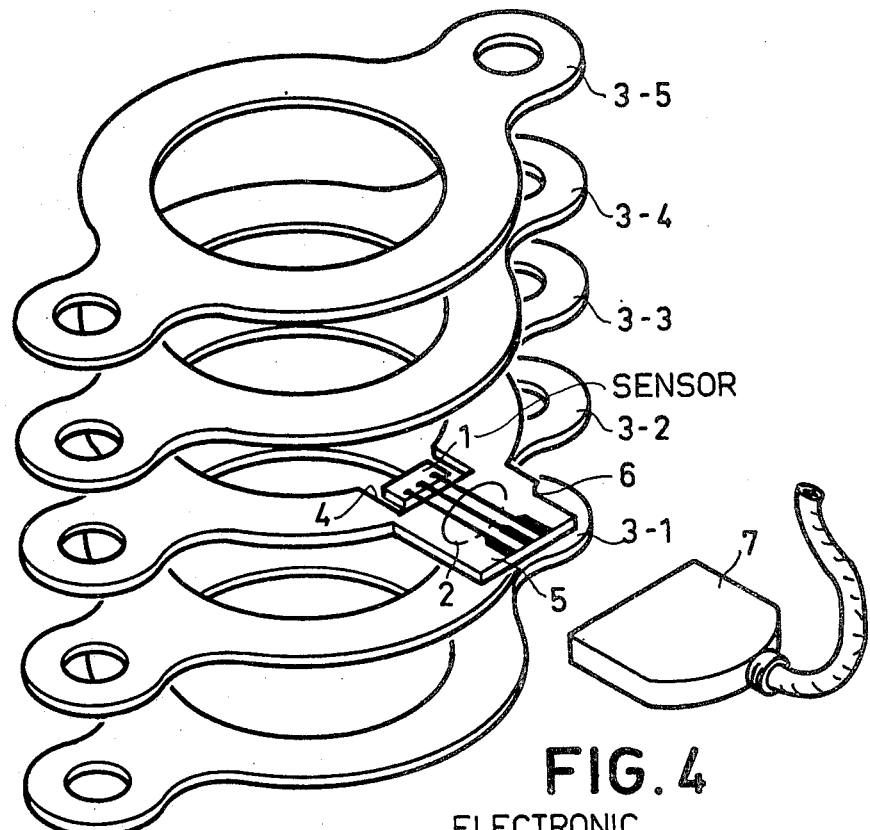

A first modified embodiment of an insertion device in accordance with the invention is illustrated in FIG. 4. The device is formed essentially by the sealing gasket located between the exhaust manifold and the exhaust pipe leading to the silencer and to the exhaust chamber. This gasket comprises in general one or more asbestos washers 3-2 to 3-4 enclosed between two metal washers 3-1 and 3-5. To prevent the sensor from being subjected to the direct aggressions of the exhaust gases, a cut-out for forming a cavity can be provided in one of the washers where the sensor is placed close to the exhaust gases flowing through the central orifice of this stack of washers, this orifice being called communication window in what follows. The connections are brought out towards the periphery of washer 3-3, which is advantageously extended by a tongue 5 provided with a cut-out 6. This arrangement allows the plugging-in of an electrical connector 7, positioned in the correct direction thanks to cut-out 6 which provides foolproof positioning.

Figure 5:
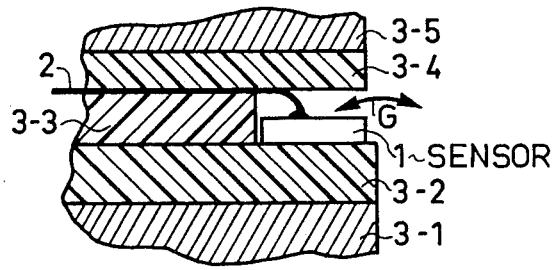
Figure 6:
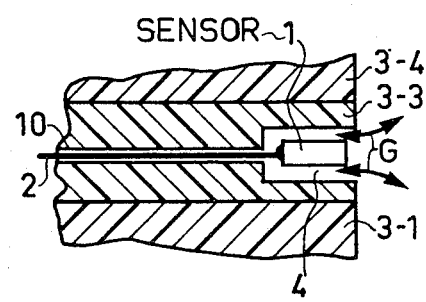

For passing the connections, two variations are illustrated in FIGS. 5 and 6. In FIG. 5, the connections are simply held by pressing between two layers 3-3 and 3-4 of the gasket. The washers forming these successive layers must have sufficient thickness to allow the exhaust gases to have free access to sensor 1. Sensors formed by thin-film depositing techniques, for example those described in U.S. Pat. No. 4,272,350, have a thickness of the order of 0.3 mm, which represents a total thickness including the connections of 1 mm. The washers may have a typical thickness of 3 mm which is reduced to 2 mm after crushing during fixing of the two assembled pipes. in FIG. 6, the cavity 4 has a thickness less than the thickness of the washer, it may be formed by extruding the material. In the thickness of this material, in a direction parallel to the plane of the washer, there are formed holes whose diameters are equal to or slightly greater than that of the wires forming the electrical connections 2. The sensor is then threaded by these connections so that these latter exit towards the periphery. After tightening of the washers, the connection wires 2 are held by the crushing of the material and the sensor is mechanically held in position.

This variation is particularly advantageous when the gasket comprises a single thick washer.

The sensor is in contact with the exhaust gases at a temperature of the order of 800° to 900° C. The periphery of the washer is at a temperature of the order of 200° C., and it is preferable to use, for electrical connections 2, a material which is slightly heat-conducting. Since the type of sensor used has a high input impedance and since the electric currents brought into play are very small, the conductivity is not critical. One example of a usable material is stainless steel.

In another variation, the sensor may be placed in the gasket located between the manifold and the exhaust ports formed in the cylinder head of the internal combustion engine. This variation has the advantage that the surface of the engine is at a lower temperature than the surface of the exhaust pipes. In fact, this temperature is of the order of 100° C. In general, when the engine comprises several cylinders and several exhaust ports, the gasket is in a single piece comprising several communication windows matching the exhaust ports. It is then advantageous, for some applications one of which will be described subsequently with reference to FIG. 11, to associate a sensor with each of these orifices. Such a variation is illustrated in FIG. 8. The gasket is in the form of a single piece 11, forming a support for inserting sensors 1-1 to 1-4.

It is also advantageous, especially for sensors constructed in accordance with the embodiment of FIG. 8, to provide at the periphery of the gasket-forming elements, a module comprising electronic circuits which provide an electric interface between the sensor and external circuits using the signals delivered by the sensors.

Figure 7:
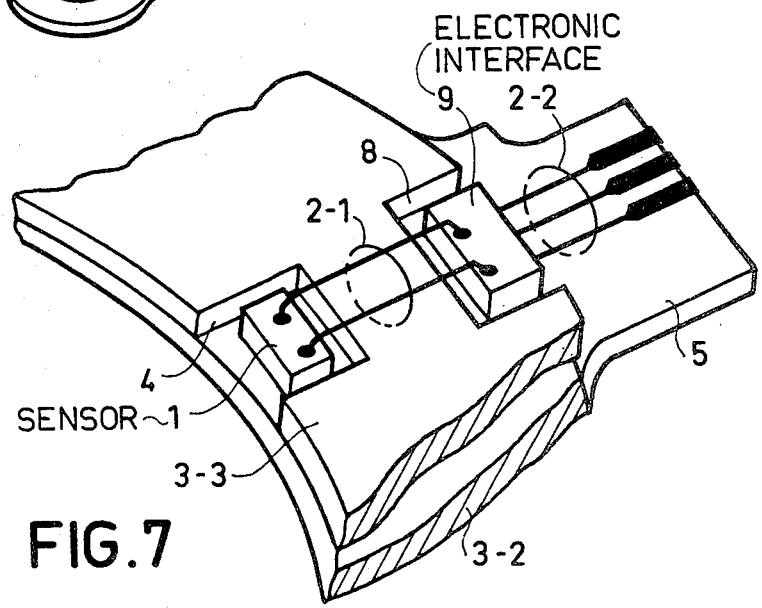

Such an arrangement is illustrated in FIG. 7. There is provided adjacent tongue 5, on which electrical connector 7 is plugged (FIG. 4), a second cavity 8 in which is placed a module 9 providing the electrical impedance-matching circuitry between the sensor, comprising a measuring cell of the concentration-stack type having a high output impedance, an external user circuits. For this, signals delivered by sensor 1 are transmitted to module 9, a hybrid integrated circuit, by means of connections 2-1 connected to the input terminals of this module. Output connections 2-2 shown by way of example as three in number convey the output signals and feed the electronic circuits of the module with electrical energy. The temperature reigning in cavity 8, in particular in the variation shown in relation to FIG. 7, is of the order of 150° C., which is compatible with the temperature resistance possibilities of certain semiconductor elements at present used.

The variations according to a first approach of the invention, presented with reference to FIGS. 3 to 8, require no transformation of the exhaust conduits and are particularly adapted for sensors having a flat structure. However, in some countries norms may force the constructors to provide at the outset standardized supports, for example threaded, for inserting a sensor into the exhaust pipes. The invention is also applicable to screwable insertion devices. One example of such an embodiment according to this approach is illustrated by FIG. 9. The device comprises two metal pieces: a first metal piece 12 having a lower flat face and provided with a driving nut 18 on its outer face; and a second metal piece 13 also having a flat face and provided on its other face with a thread 19 intended to be inserted by screwing into the mating member 16 provided in the exhaust pipe 15. The device of the invention provides for example two gaskets 30 and 31 between which the sensor 1 will be held by clamping by means of its connections 2. Element 30 is provided with a window 40 giving onto a channel 14 provided in metal piece 13 so as to place the sensor in communication with the exhaust gases. One of the elements of the stack also comprises a projecting tongue 5, onto which a connector may be plugged (as in the case of FIG. 4). Furthermore, means for fixing, for example by means of screw 17, are provided. Elements 30 and 31 form a sealing gasket and may be made from asbestos, similarly to the sealing gasket for the exhaust pipes described above. This device of the invention, made from an inexpensive material, has then a very simple structure well-adapted to the flat geometry of the senor 1. A matching module, as in the case of FIG. 7, may also be provided.

Figure 10:
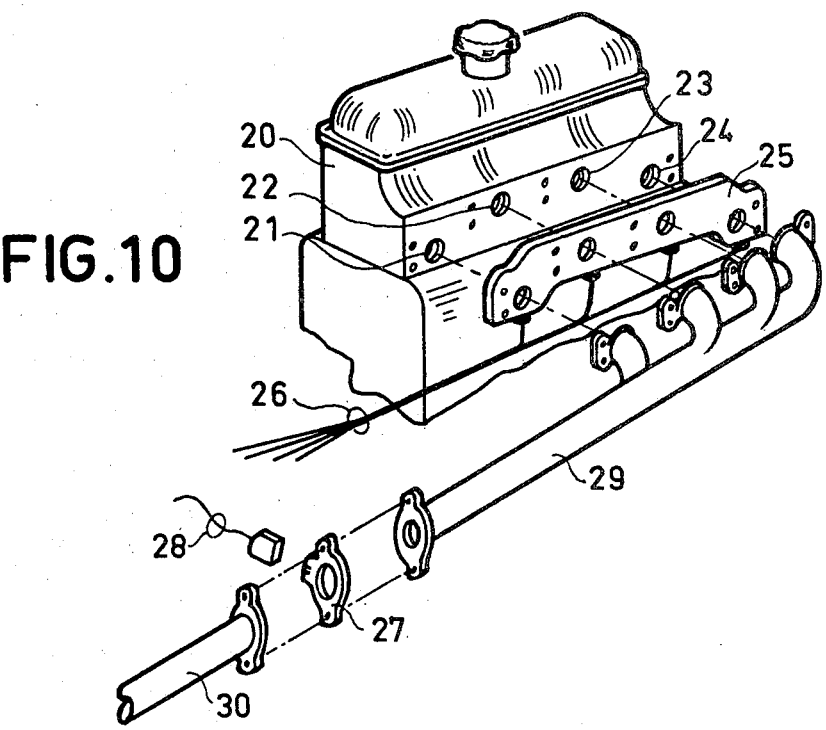
FIG. 10 illustrates the fitting of insertion devices of the invention into the exhaust conduits of an internal combustion engine.

FIG. 10 illustrates two possibilities for mounting insertion devices in accordance with the variations of FIGS. 3 to 8. By way of example, the internal combustion engine 20 has four cylinders and exhaust ports 21 to 24, one per cylinder. According to the variation described in connection with FIG. 7, the insertion device comprises four sensors and in this case forms a gasket between the cylinder head and the exhaust manifold 29. The outputs of these sensors are transmitted to external circuits not shown by means of cable 26. The sensor may also be inserted, for example by means of an insertion device described in connection with FIG. 4, between the manifold 29 and the exhaust pipe 30. The signals delivered by the sensor associated with device 27 are conveyed by cable 28.

Figure 11:
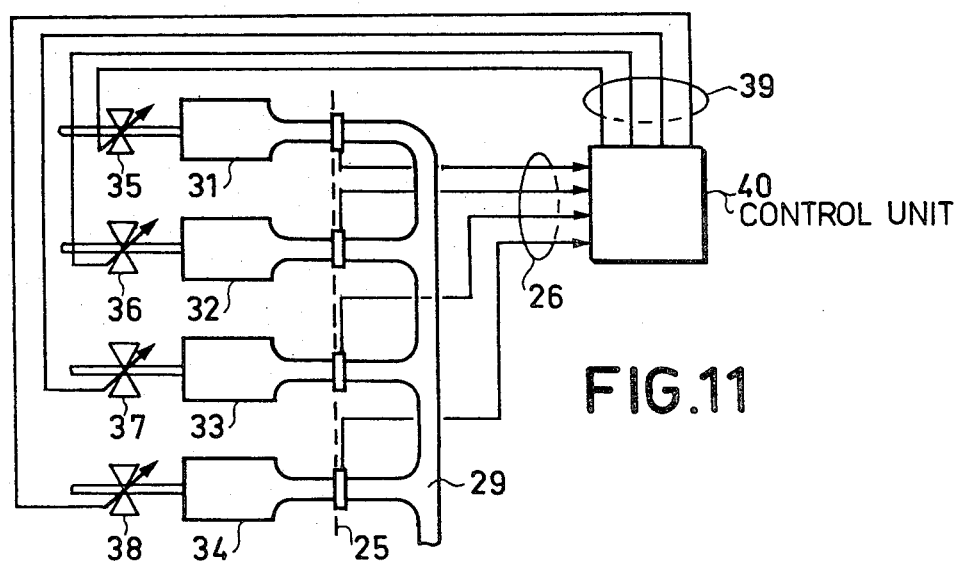
FIG. 11 illustrates the regulation of the injection of fuel into the cylinders of an internal combustion engine using sensors inserted into the exhaust conduits by means of a device in accordance with the invention.

In FIG. 11 is shown an example of applying sensors to controlling the injection or more generally the amount of fuel admitted into the cylinders of an internal combustion engine and using an insertion device according to the variation described in connection with FIG. 7. The exhaust gases of each of the cylinders may in fact be advantageously analyzed individually. These cylinders, four in number in the example considered, are shown symbolically be references 31 to 34. The insertion device, also comprising four sensors and forming a sealing joint between the exhaust ports formed in the cylinder head of the engine and the exhaust manifold 29, is shown by the reference 25. This device is similar to the one shown in FIG. 10. The signals delivered by the four sensors are transmitted by means of cable 26 to user circuits 40. Each fuel intake is provided with an individually adjustable injector or carburetor 35 to 38.

The circuits 40 using the signals delivered by these sensors elaborate four control signals used for the individual adjustment of these injectors. The control of the injectors may be effected electrically, as suggested by reference 39 in FIG. 11, or by any other appropriate means, in particular by a mechanical coupling, which is generally the case for a carburetor. The processes used for this regulation are outside the scope of the invention and will not be described further. The insertion device, and in particular the variation shown in connection with FIG. 7, is particularly adapted to the application illustrated by FIG. 11, for it allows optimum insertion of the sensors for revealing the individual operational parameters of each of the cylinders.

The measurements supplied by the sensors may be also weighted and a single member controlled for controlling the amount of fuel, particularly in the most widespread case of engines fed from a single carburetor. This method has the advantage that the engine may continue to operate even in the case of a breakdown of one of the sensors (breakage of an electrical connection).

The invention is not limited to the embodiments which have just been described. Materials may be used other than asbestos which is generally used for forming the sealing gaskets of exhaust pipes. The invention is not limited either to motor vehicles but may be applied to all machines having an internal combustion engine, whatever the number of cylinders. Sensors, other than those using a measuring cell of the concentration-stack type may be inserted by means of devices in accordance with the invention. There may be mentioned, in a way which is in no wise limiting, sensors using a resistance variation or thermocouple sensors.

What is claimed as new and desired to be secured by Letters Patent of the United States is:

1. A device for supporting at least one sensor in at least one exhaust conduit of an internal combustion engine having a cylinder head and at least one exhaust port each, said sensor being adapted to measure at least one parameter of the exhaust gasses in said conduit and including output leads conveying electrical signals representative of said parameters, said device comprising:
   a flat element formed by at least one sheet of insulating and compressible material resistant to high temperatures;
   fixing means for fixing said flat element in a gas tight manner between two pieces of each said exhaust conduit;
   a first aperture having walls defined by said flat element, said first aperture being coaxial with, and having the same dimensions as, said exhaust conduit, whereby said flat element forms a gasket in said exhaust conduit;
   at least one first cavity having walls defined by said flat element and extending to said first aperture, whereby each said first cavity communicates with said exhaust conduit but is out of the flow path of gasses in said exhaust conduit, each said first cavity being adapted to support said sensor; and
   means associated with said flat element for rigidly supporting said leads of each said sensor, whereby each said sensor is rigidly held in one said first cavity.

2. The device as claimed in claim 1, wherein said flat element further comprises at least one tongue projecting radially therefrom and wherein said leads of each said sensor are made integral with one said tongue so that an electrical connector may be plugged on said tongue to provide electrical connections with external devices using electrical signals delivered by said sensor.

3. The device as claimed in claim 2, wherein, adjacent the tongue, a second cavity is provided in said flat element so as to dispose therein electrical impedance-matching circuits; said circuits comprising input terminals connected to said leads of said sensor and output terminals connected to connections integral with said tongue.

4. The device as claimed in claim 1 wherein, with the exhaust conduits comprising an exhaust manifold and an exhaust pipe, said two pieces of said exhaust conduits are formed respectively by said exhaust manifold and said exhaust pipe.

5. The device as claimed in claim 1 wherein, said two pieces of said exhaust conduits comprise said cylinder head and said exhaust manifold.

6. The device as claimed in claim 5 wherein, with said internal combustion engine comprising several cylinders each having an exhaust port formed in said cylinder head, said element comprises as many windows as said exhaust ports, and wherein with each of said windows there is associated a sensor.

7. The device as claimed in claim 1, wherein the material forming said element is asbestos.

8. A system for controlling the amount of fuel in an internal combustion engine having several cylinders, associated with an insertion device as claimed in claim 6 comprising one sensor per cylinder and wherein the output signals of said sensors are used for adjusting the amount of fuel.

* * * * *